US00PP19504P2

(12) United States Plant Patent
von Danwitz

(10) Patent No.: US PP19,504 P2
(45) Date of Patent: Nov. 25, 2008

(54) POINSETTIA PLANT NAMED 'ICE PUNCH'

(50) Latin Name: *Euphorbia pulcherrima*
Varietal Denomination: Ice Punch

(76) Inventor: Marita von Danwitz, Anrather Strasse 76, D-47918 Tönisvorst (DE)

( * ) Notice: Subject to any disclaimer, the term of this patent is extended or adjusted under 35 U.S.C. 154(b) by 235 days.

(21) Appl. No.: 11/415,487

(22) Filed: May 1, 2006

(51) Int. Cl.
*A01H 5/00* (2006.01)

(52) U.S. Cl. ..... Plt./303

(58) Field of Classification Search ..... Plt./303
See application file for complete search history.

(56) References Cited

PUBLICATIONS

PBR 20050332—filed Feb. 21, 2005, published Apr. 15, 2005.*
Google print–out dated Jan. 6, 2008—www/pla–int.com—2 pages.*

* cited by examiner

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of Poinsettia plant named 'Ice Punch', characterized by its uniform, upright, compact and mounded plant habit; freely branching habit; dark green-colored leaves; mid-season flowering response; inflorescences with cherry red and pink bi-colored flower bracts; and excellent post-production longevity.

1 Drawing Sheet

Botanical designation: *Euphorbia pulcherrima.*
Cultivar denomination: 'Ice Punch'.

BACKGROUND OF THE INVENTION

The present invention relates to a new and distinct cultivar of Poinsettia plant, botanically known as *Euphorbia pulcherrima* Willd., and hereinafter referred to by the name 'Ice Punch'.

The new Poinsettia is a naturally-occurring branch mutation of the Poinsettia cultivar Eckabish, disclosed in U.S. Plant Pat. No. 11,200. The new Poinsettia was discovered and selected by the Inventor in a controlled environment in Tönisvorst, Germany. The new Poinsettia was selected on the basis of its unique flower bract coloration.

Asexual reproduction of the new cultivar by terminal vegetative cuttings propagated in a controlled environment in Tönisvorst, Germany, has shown that the unique features of this new Poinsettia are stable and reproduced true to type in successive generations of asexual reproduction.

SUMMARY OF THE INVENTION

The cultivar Ice Punch has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Ice Punch'. These characteristics in combination distinguish 'Ice Punch' as a new and distinct cultivar of Poinsettia.

1. Uniform, upright, compact and mounded plant habit.
2. Freely branching habit.
3. Dark green-colored leaves.

4. Mid-season flowering response; under natural season conditions, plants flower in about 8.5 weeks in Encinitas, Calif.
5. Inflorescences with cherry red and pink bi-colored flower bracts.
6. Excellent post-production longevity.

In side-by-side comparisons conducted in Encinitas, Calif., plants of the new Poinsettia differed from plants of the parent, the cultivar Eckabish, primarily in flower bract coloration as plants of the cultivar Eckabish have solid cherry red-colored flower bracts.

Plants of the new Poinsettia can be compared to plants of the Poinsettia cultivar 490 Marble, disclosed in U.S. Plant Pat. No. 8,833. In side-by-side comparison conducted in Encinitas, Calif., plants of the new Poinsettia differed from plants of the cultivar 490 Marble primarily in flower bract coloration as plants of the cultivar 490 Marble have light pink and pale yellow-colored flower bracts.

BRIEF DESCRIPTION OF THE PHOTOGRAPHS

The accompanying photographs illustrate the overall appearance of the new Poinsettia. These photographs show the colors as true as it is reasonably possible to obtain in colored reproductions of this type. Colors in the photographs may differ slightly from the color values cited in the detailed botanical description which accurately describe the colors of the new Poinsettia.

The photograph at the bottom of sheet comprises a side perspective view of a typical flowering plant of 'Ice Punch' grown in a container.

The photograph at the top of the sheet comprises a close-up view of typical inflorescences of 'Ice Punch'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Encinitas, Calif. during the spring in a polyethylene-covered greenhouse and under conditions and practices which approximate those generally used in commercial Poinsettia production. During the production of the plants, day temperatures averaged 24° C., night averaged 19° C. and light levels were about 4,000 foot-candles. Measurements and numerical values represent averages for typical flowering plants. Single plants were grown in 16.5-cm pots and pinched one time. Plants were about 14 weeks old when the photographs and the detailed description were taken.

Botanical classification: *Euphorbia pulcherrima* cultivar Ice Punch.

Parentage: Naturally-occurring branch mutation of *Euphorbia pulcherrima* cultivar Eckabish, disclosed in U.S. Plant Pat. No. 11,200.

Propagation:

*Type.*—Terminal vegetative cuttings.

*Time to initiate roots.*—About ten days.

*Time to produce a rooted young plant.*—About four weeks.

*Root description.*—Fibrous; white in color.

Plant description:

*Plant habit and form.*—Uniform, upright, compact and mounded plant habit; inverted triangle. Inflorescences positioned above the foliage plane. Moderately vigorous growth habit.

*Plant height.*—About 25 cm.

*Plant diameter or spread.*—About 35 cm.

*Lateral branch description.*—Quantity: Freely branching habit, about ten lateral branches develop after pinching. Length: About 19 cm. Diameter: About 4 mm. Internode length: About 2 cm. Strength: Strong. Texture: Smooth, glabrous. Color: 146A.

*Foliage description.*—Arrangement: Alternate, simple. Length: About 9.7 cm. Width: About 9 cm. Shape: Ovate to oak leaf. Apex: Acuminate. Base: Acute. Margin: Entire with typically two lobes per lateral edge. Venation pattern: Pinnate. Texture, upper surface: Smooth, glabrous. Texture, lower surface: Minute pubescence. Surface: Rugose. Aspect: Mostly flat to folded upright along the midvein. Color: Developing foliage, upper surface: 147A. Developing foliage, lower surface: 147B. Fully expanded foliage, upper surface: Darker than 147A; venation, 147C. Fully expanded foliage, lower surface: More gray than 147B; venation, 147D. Petiole: Length: About 5.5 cm. Diameter: About 2 mm. Texture, upper and lower surfaces: Smooth, glabrous. Color, upper and lower surfaces: 182A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Mid-season flowering; response time, about 8.5 weeks; natural season flowering maturity date is early December for plants grown in Encinitas, Calif.

*Post-production longevity.*—Excellent post-production longevity; plants of the new Poinsettia maintain good substance and bract color for about four weeks under interior conditions.

*Inflorescence size.*—Diameter: About 20 cm. Height (depth): About 4 cm.

*Flower bracts.*—Quantity per inflorescence: About 18. Length, largest bracts: About 10 cm. Width, largest bracts: About 9.2 cm. Shape: Mostly elliptic. Apex: Acuminate. Base: Acute to attenuate. Margin: Entire with irregular lobing. Texture, upper and lower surfaces: Smooth, glabrous. Surface: Slightly rugose. Aspect: Upright to flat to slightly folded upright along midvein; slightly recurved. Venation pattern: Pinnate. Color: Developing or transitional bracts, upper surface: 53B. Developing or transitional bracts, lower surface: 47A. Fully developed bracts, upper surface: Towards the margins, slightly more red than 47A; irregular central area, 47C to 47D, color becoming closer to 39C with development. Fully developed bracts, lower surface: Towards the margins, 46B; irregular central area, 48C. Venation, upper and lower surfaces: Similar to flower bract color. Bract petiole: Length: About 4.2 cm. Diameter: About 1.5 mm. Texture, upper and lower surfaces: Smooth, glabrous. Color, upper and lower surfaces: 182B to 182C.

*Cyathia.*—Quantity per corymb: About eight to ten. Diameter of cyathia cluster: About 2.2 cm. Length: About 1 cm. Width: About 6 mm. Shape: Ovoid. Color, immature: 145A. Color, mature: 145A to 145B. Nectaries: Quantity per cyathium: About one or two. Size: About 2 mm by 5 mm. Color: 17A.

*Peduncles.*—Length: About 3 mm. Diameter: About 2 mm. Strength: Strong. Aspect: Upright. Texture: Smooth, glabrous. Color: 145A.

*Reproductive organs.*—Stamens: Quantity per cyathium: About 20. Anther shape: Oval. Anther length: Less than 1 mm. Anther color: 185A. Amount of pollen: Moderate. Pollen color: 14A. Pistils: None observed. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15.5° C. to about 30° C.

It is claimed:

1. A new and distinct Poinsettia plant named 'Ice Punch' as illustrated and described.

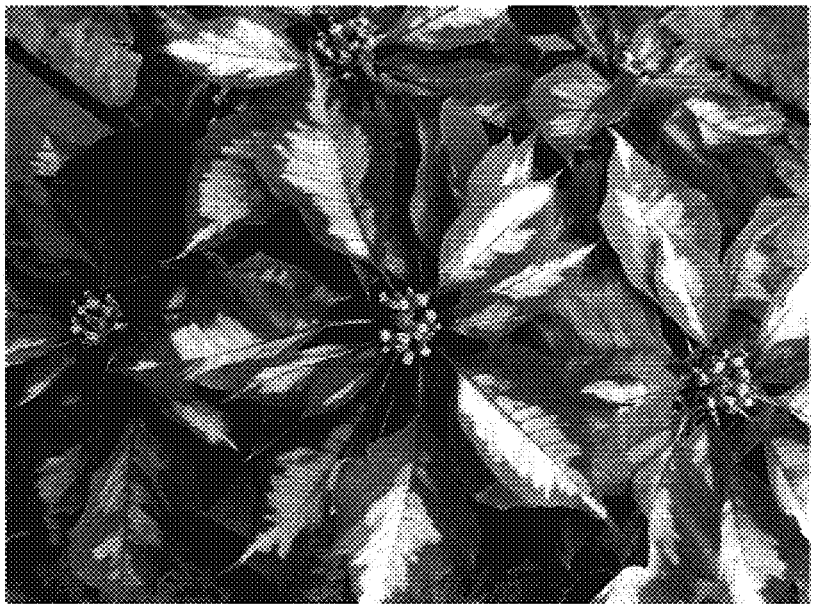
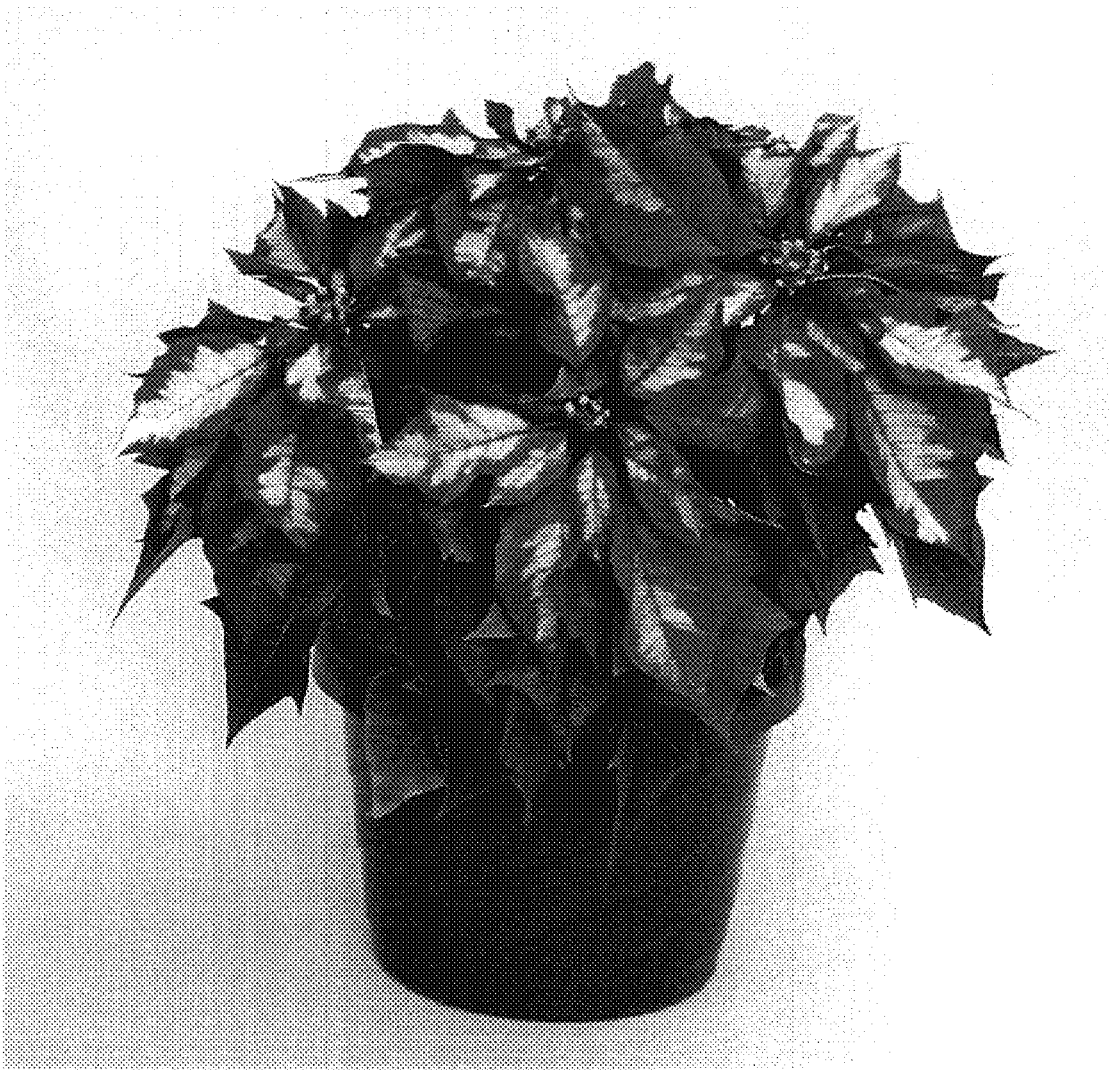

* * * * *